US007335741B2

(12) United States Patent
Stein et al.

(10) Patent No.: US 7,335,741 B2
(45) Date of Patent: Feb. 26, 2008

(54) MEANS FOR USE IN DIAGNOSTICS AND/OR THERAPY

(76) Inventors: Harald Stein, Balbronner Strasse 3, Berlin (DE) 14195; Horst Durkop, Schlehdornsteig 17, Berlin (DE) 14129

( * ) Notice: Subject to any disclaimer, the term of this patent is extended or adjusted under 35 U.S.C. 154(b) by 141 days.

(21) Appl. No.: 10/612,832

(22) Filed: Jul. 1, 2003

(65) Prior Publication Data

US 2005/0009769 A1 Jan. 13, 2005

(30) Foreign Application Priority Data

Jul. 1, 2002 (DE) ................................ 102 29 475
Jul. 9, 2002 (DE) ................................ 102 30 909

(51) Int. Cl.
*C07K 16/00* (2006.01)
*C12N 5/06* (2006.01)
*C12N 9/96* (2006.01)

(52) U.S. Cl. ................................ 530/387.1; 530/388.1; 435/326; 435/188

(58) Field of Classification Search .............. 530/387.1
See application file for complete search history.

(56) References Cited

U.S. PATENT DOCUMENTS 6,033,876 A * 3/2000 Lemke et al. .............. 435/69.6
2002/0064527 A1* 5/2002 Mohler et al. ........... 424/144.1
2004/0018194 A1* 1/2004 Francisco et al. ........ 424/144.1

FOREIGN PATENT DOCUMENTS

WO WO 94/04189 3/1994

OTHER PUBLICATIONS

Deonarain MP, Epenetos AA. Targeting enzymes for cancer therapy: old enzymes in new roles.Br J Cancer. Nov. 1994;70(5):786-94.*

Gravekamp C, Horensky DS, Michel JL, Madoff LC. Variation in repeat number within the alpha C protein of group B streptococci alters antigenicity and protective epitopes Infect Immun. Sep. 1996;64(9):3576-83.*

Dong et al., J of Molecular Recognition, vol. 16 p. 28-36, 2003.*

Capra, et al., *Immunology Today*, vol. 3 (1982), pp. 332-339.

Terenzi, et al. "Anti-CD30 (BER-H2) immunotoxins containing the type 1 ribosome- inactivating proteins momordin and PAP-S (pokeweed antiviral protein from seeds) display powerful antitumour activity against $CD30^+$ tumour cells in vitro and in SCID mice"; *British Journal of Haematology* (1996) 92: 872-879.

Cheong, et al. "Affinity enhancement of bispecific antibody against two different epitopes in the same antigen"; *Biochemical and Biophysical Research Communications*; vol. 173, No. 3, (1990), 795-800.

Lu, et al., "Acquired antagonistic activity of a bispecific diabody directed against two different epitopes on vascular endothelial growth factor receptor 2"; *Journal of Immunological Methods*; 230 (1999) 159-171.

Klimka, et al. "Human anti-CD30 recombinant antibodies by guided phage antibody selection using cell panning"; *British Journal of Cancer* (2000) 83(2), 252-260.

Dong, et al. "Human CD30: Structural implications from epitope mapping and modeling studies"; *J. Mol. Recogait* (2003); 16: 28-36.

Dürkop, et al. "Structure of the Hodgkin's lymphoma-associated human CD30 gene and the influence of a microsatellite region on its expression in $CD30^+$ cell lines"; *Biochimica et Biophysica Acta*; 1519 (2001); 185-191.

Hansen, et al. "Ectodomain shedding of CD30 is specifically regulated by peptide motifs in its cysteine-rich domains 2 and 5"; *The FASEB Journal*; Express Article 10.1096/fg.03-0901 fje. Published online Mar. 19, 2004.

* cited by examiner

*Primary Examiner*—Shanon Foley
*Assistant Examiner*—Lei Yao
(74) *Attorney, Agent, or Firm*—Townsend and Townsend and Crew LLP

(57) ABSTRACT

The present invention relates to a specific reagent for the detection of the CD30 molecule, whereby this reagent is suitable in particular for the diagnosis of lymphomas.

11 Claims, 4 Drawing Sheets

SEQUENCE LISTING

```
<160> NUMBER OF SEQ ID NOS: 12

<210> SEQ ID NO 1
<211> LENGTH: 17
<212> TYPE: DNA
<213> ORGANISM: Artificial
<220> FEATURE:
<221> NAME/KEY: misc_feature
<223> OTHER INFORMATION: Primer A-C(K)

<400> SEQUENCE: 1

agatggatac agttggt                                                17


<210> SEQ ID NO 2
<211> LENGTH: 17
<212> TYPE: DNA
<213> ORGANISM: Artificial
<220> FEATURE:
```

-continued

<221> NAME/KEY: misc_feature
<223> OTHER INFORMATION: Primer A-C(H)1

<400> SEQUENCE: 2
ggggccagtg gatagac 17

<210> SEQ ID NO 3
<211> LENGTH: 15
<212> TYPE: DNA
<213> ORGANISM: Artificial
<220> FEATURE:
<221> NAME/KEY: misc_feature
<223> OTHER INFORMATION: Primer B(NotI)

<400> SEQUENCE: 3
gcgcggccgc ggagg 15

<210> SEQ ID NO 4
<211> LENGTH: 29
<212> TYPE: DNA
<213> ORGANISM: Artificial
<220> FEATURE:
<221> NAME/KEY: misc_feature
<223> OTHER INFORMATION: Primer C(NotI)

<400> SEQUENCE: 4
gcgcggccgc ggaggccccc ccccccccc 29

<210> SEQ ID NO 5
<211> LENGTH: 25
<212> TYPE: DNA
<213> ORGANISM: Artificial
<220> FEATURE:
<221> NAME/KEY: misc_feature
<223> OTHER INFORMATION: Primer D-C(K EcoRI)

<400> SEQUENCE: 5
ggaattcgga tacagttggt gcagc 25

<210> SEQ ID NO 6
<211> LENGTH: 24
<212> TYPE: DNA
<213> ORGANISM: Artificial
<220> FEATURE:
<221> NAME/KEY: misc_feature
<223> OTHER INFORMATION: Primer D-C(H [\m]EcoRI)

<400> SEQUENCE: 6
ggaattcgtg gatagacaga tggg 24

<210> SEQ ID NO 7
<211> LENGTH: 35
<212> TYPE: DNA
<213> ORGANISM: Artificial
<220> FEATURE:
<221> NAME/KEY: misc_feature
<223> OTHER INFORMATION: Primer E-(K SalI)

<400> SEQUENCE: 7
gatcgtcgac ggaaatgcat cagaccagca tgggc 35

-continued

<210> SEQ ID NO 8
<211> LENGTH: 35
<212> TYPE: DNA
<213> ORGANISM: Artificial
<220> FEATURE:
<221> NAME/KEY: misc_feature
<223> OTHER INFORMATION: Primer E-(H SalI)

<400> SEQUENCE: 8
catagtcgac aatacgatca gcatcctctc cacag 35

<210> SEQ ID NO 9
<211> LENGTH: 35
<212> TYPE: DNA
<213> ORGANISM: Artificial
<220> FEATURE:
<221> NAME/KEY: misc_feature
<223> OTHER INFORMATION: Primer F(K NotI)

<400> SEQUENCE: 9
atcagcggcc gcacttaaca aggttagact tagtg 35

<210> SEQ ID NO 10
<211> LENGTH: 38
<212> TYPE: DNA
<213> ORGANISM: Artificial
<220> FEATURE:
<221> NAME/KEY: misc_feature
<223> OTHER INFORMATION: Primer F-(H NotI)

<400> SEQUENCE: 10
gatagcggcc gcatgcattt agaatgggag aagttagg 38

<210> SEQ ID NO 11
<211> LENGTH: 13
<212> TYPE: PRT
<213> ORGANISM: Artificial
<220> FEATURE:
<221> NAME/KEY: misc_feature
<223> OTHER INFORMATION: Spot 16

<400> SEQUENCE: 11

Asp Cys Arg Lys Gln Cys Glu Pro Asp Tyr Tyr Leu Asp
1 5 10

<210> SEQ ID NO 12
<211> LENGTH: 13
<212> TYPE: PRT
<213> ORGANISM: Artificial
<220> FEATURE:
<221> NAME/KEY: misc_feature
<223> OTHER INFORMATION: Spot 74

<400> SEQUENCE: 12

Gly Asp Cys Arg Lys Gln Cys Glu Pro Asp Tyr Tyr Leu
1 5 10

MEANS FOR USE IN DIAGNOSTICS AND/OR THERAPY

FIELD OF INVENTION

The present invention relates to a reagent for use in diagnostics and/or therapy, a cell ich produces the named reagent and methods using the reagent.

BACKGROUND OF INVENTION

The primary diagnosis of CD30-positive tumour diseases is currently carried out on an immunohistological basis, with only reagents from mice e.g. Ber-H2 being used at present as the antibody. This reagent is a monoclonal antibody directed at the CD30 molecule which was described in 1987 in a short article and in 1989 more detailed (Schwarting et al., Ber-H2; a new anti-Ki-1 (CD30) monoclonal antibody directed at a formol-resistant epitope, Blood, 74:1678-1689, 1989). This antibody is secreted by the mouse myeloma hybrid cell line of the same name. However, it is a considerable disadvantage, in the mass production of this antibody in a long-term culture (in fermenters, for example), that the antibody-producing cells are often, after just a few generations, overgrown by cells which have lost the ability to produce antibodies, obviously because the latter are no longer able to synthesise heavy immunoglobulin chains or also heavy and light immunoglobulin chains.

The propagation diagnosis of the tumour diseases mentioned above is generally carried out by computer tomography, sonography and/or lymphography. The non-invasive propagation diagnosis mentioned, however, is associated with the disadvantage that only relatively large tumour masses can be identified, but that smaller tumours or metastases are not detectable. The surgical propagation diagnosis methods that are therefore often used in addition are a major burden on the patient and are limited to particular body cavities (e.g. abdominal cavities). The standard treatment of CD30-positive tumours which is currently the only medically accepted treatment and thus the only treatment used is carried out using non-specific radio and/or chemotherapy. Although the success rate is approx. 60-70%, there is so far no curative concept for those for whom therapy fails.

For this reason, the monoclonal antibody Ber-H2 was conjugated with vegetable toxins and used experimentally for the treatment of patients with Hodgkin's disease in the terminal phase of the disease (Falini et al., Response of refractory Hodgkin's disease to monoclonal anti-CD30 immunotoxin, *Lancet,* 339:1195-1196, 1992). The four patients treated showed a reduction in tumour mass of 50% to almost 100% within ten days. However, in all cases, after a varying amount of time, the tumours reappeared at the old and/or new locations. It was not possible to repeat the immunotoxin application because the patients, without exception, had already formed antibodies against the mouse antibody Ber-H2.

As such, immunotoxins have already been used experimentally in vivo in humans which have enabled Hodgkin's lymphoma cells to be recognised or eliminated (e.g. Falini et al., Response of refractory Hodgkin's disease to monoclonal anti-CD30 immunotoxin, *Lancet,* 339:1195-1196, 1992; Falini et al., In vivo targeting of Hodgkin and Reed-Stemberg cells of Hodgkin's disease with monoclonal antibody Ber-H2(CD30): Immunohistological evidence, *Brit. J. Haematol.,* 82:38-45, 1992).

Further, it has been possible to show that the CD30 molecule is expressed in vitro and in vivo selectively by activated $T_H2$ blasts (Romagnani S., Induction of $T_H1$ and $T_H2$ responses: a key role for the 'natural' immune response?, *Immunol. Today,* 13:379-381, 1992) (Del Prete et al., CD30 Th2 cytokines and HIV infection: a complex and fascinating link, *Immunol. Today,* 16:76-80, 1995). In patients with allergic diseases, the number of $CD30^+$ $T_H2$ blasts was much higher than in normal people. It is therefore conceivable that a majority of autoaggressive diseases are due to a miscontrol of the $T_H$ response with an increase in the number of $T_H2$ cells. Thus it should also be possible to use the CD30 molecule as a target in the diagnosis and/or treatment of inflammatory diseases.

However, there remains a need for improved CD30 molecules for use in, e.g., diagnosis and treatment.

BRIEF SUMMARY OF THE INVENTION

The object of the present invention is to provide ways and means for the most efficient diagnosis and therapy possible which would also, in particular, be less susceptible to changes in the target molecule in question as a point of attack for diagnosis and/or therapy by mutations.

This object is solved according to the invention by a reagent which, at least two spatially separated positions of a cell-bound or soluble molecule such as, for example, a tumour marker (tumour antigen), enters into an interaction with the latter or the nucleic acid coding for this.

(A) Spot analysis using a complete set of tridecamer peptides which are derived from the extracellular part of the CD30 molecule after incubation with the antibody according to the invention, followed by marked reagents which recognise this.

(B) Analysis of the epitope of the antibody according to the invention by substitution of every individual residue of the sequence in Spot 74 (left column, identical peptides as controls) with all 20 L amino acids (upper line).

Figure 4:
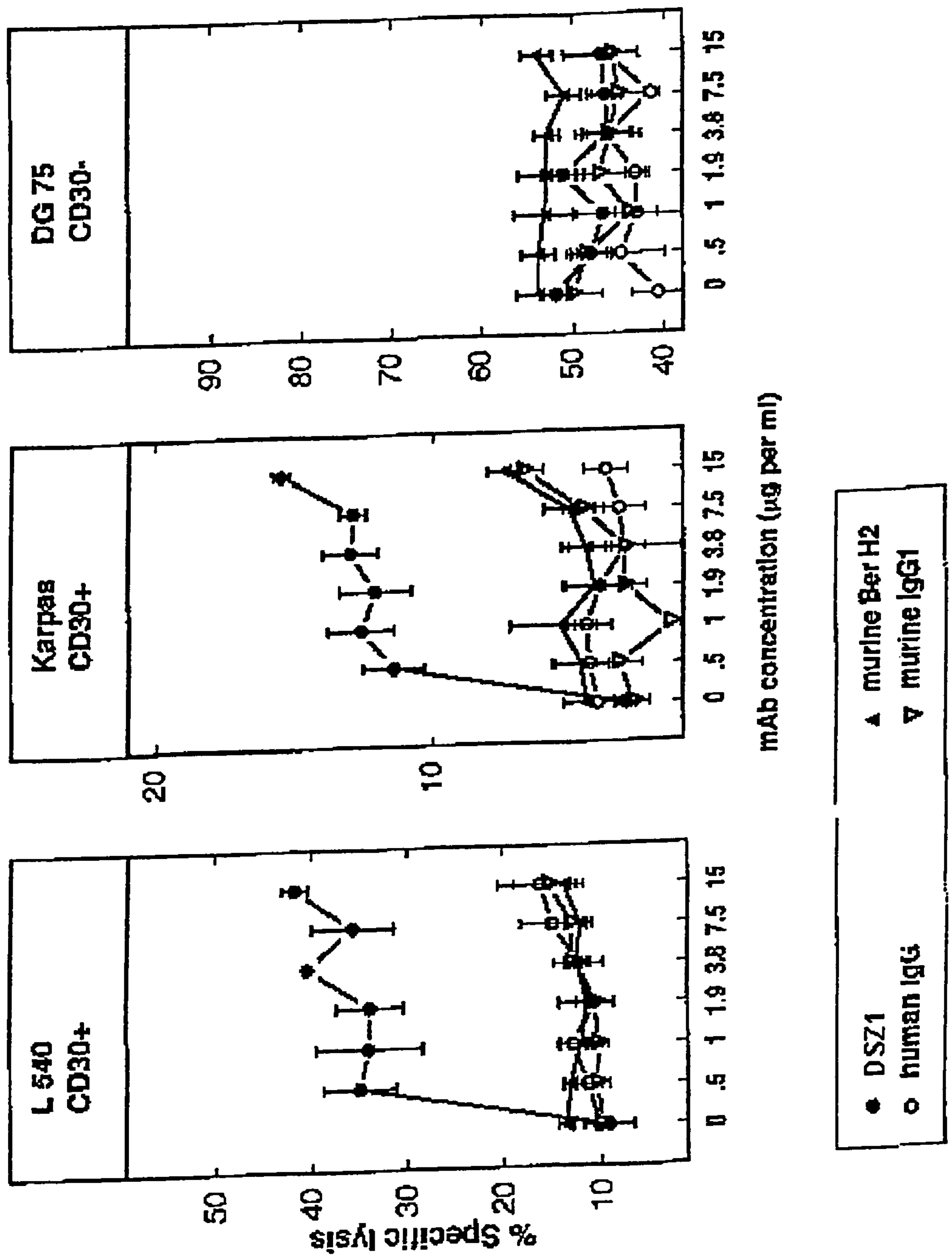

FIG. 4 shows the antibody secreted by the cell line DSZ1 according to the invention provides the ADCC. Peripheral blood cells from healthy donors were stimulated to produce lymphokine-activated killer cells and cytokine-induced killer cells and also stimulated monocytes. These stimulated cells were used as effectors in the presence of the antibody according to the invention against the $CD30^+$ target cell lines (L540, HDLM2, Karpas 299 and JB6) and the $CD30^-$ target cell lines (DG75 and SUP-T1) in an effector-target ratio between 30:1 and 5:1. The results with the lines L540, Karpas 299 and DG75 with the effector-target ratio of 30:1 are shown. Average values from triple determinations and standard deviations are shown. The specific cell lysis caused by the antibody was compared with the spontaneous cell lysis by means of a reference antibody, whereby human immunoglobulin and IgG1 from mice were used, amongst others, as the reference. The results with the $CD30^{+}$ cell lines HDLM2 and JB6 were very similar to the results with the $CD30^{+}$ cell lines L540 and Karpas 299, whilst the $CD30^{-}$ cell line SUP-T1, like DG75, gave no specific lysis with the antibody according to the invention.

DETAILED DESCRIPTION OF THE INVENTION

In the diagnosis and treatment of, for example, tumours, increasing use is made of antigens as target molecules as proof or as the point of attack for pharmaceutical active substances. In both cases, it is desirable that the target molecule is recognised as specifically as possible by the reagents used in order, for example, to keep incorrect diagnoses or side effects in therapy as low as possible. An example of a suitable antigen is the CD30 molecule, which only occurs extremely rarely in the normal mammal organism, but which is expressed in large numbers on tumour cells of lymphomas, especially Hodgkin's lymphoma. A general problem in diagnosis and also in therapy using certain proteins is caused by the fact that mutations may occur in the target molecules and that these molecules can thus avoid detection, in some circumstances, by a previously specific reagent. If the mutation affects an epitope, for example, which has been recognised by an originally used reagent, the mutation can lead to the recognition of the antigen by the reagent being lost. This type of change in the structure of a target molecule thus causes problems both in diagnosis and in therapy.

In addition, it is desirable for diagnosis and therapy to be carried out with the lowest possible use of reagent. This is an advantage firstly in view of the costs and secondly to achieve the goal of causing the fewest possible side effects within the treatment.

Tumour antigens are generally molecules which are expressed by tumour cells in certain stages of development, frequently appearing as surface proteins. The reagent according to the invention possesses advantageous properties in respect of reagents which are known from the state of the art in that the reagent according to the invention recognises at least two binding sites of the target molecule, e.g. a tumour marker. This means that, if mutation occurs, there is a much lower risk that the target completely loses its ability to be recognised by the reagent. With reagents known from the state of the art, there is a high risk of this; if the mutation affects the binding site of the reagent—either directly (e.g. within the epitope) or indirectly (e.g. by a conformation change)—this can lead to the loss of recognisability of the target by the reagent. Ultimately, the consequence is that the reagent no longer enters into an interaction with the target, and this means, in diagnostics, that an incorrectly negative result is produced and that therapy could fail completely, since an attack on the target cell, e.g. tumour cell, is no longer conveyed by the reagent. Because the reagent according to the invention enters into an interaction with the target at least two positions, the loss of one of the binding sites—for example by a mutation—does not lead to the complete loss of recognition of the target by the reagent; in such a case, the reagent still reacts with the second binding site. This characteristic of the reagent also results in a clearly increased reliability of the diagnosis.

Suitable positions of epitopes for recognition by a reagent according to the invention can be identified, for example, by the fact that an attempt is made to inhibit the reaction of a reagent by means of a series of short peptides which correspond to particular areas of the target molecule (Seitz, C., et al., The monoclonal antibody HCA2 recognizes a broadly shared epitope on selected classical as well as several non-classical HLA class I molecules. *Molec. Immunol.* 35:819-827, 1998). A further possibility is to allow the reagent to react with membrane-bound peptides which correspond to overlapping potential epitopes of the target molecule (Frank, R., Spot synthesis: an easy technique for the positionally addressable, parallel chemical synthesis on a membrane support. *Tetrahedron* 48:9217-9232, 1996; Kramer, A., et al., Combinatorial cellulose-bound peptide libraries: Screening tools for the identification of peptides that bind ligands with predefined specificity. *Comp. Meth. Enzymol.* 6:388-395, 1994).

Once the suitable position is known, the expert can use many methods to produce the reagent directed at the position in question (cf. e.g. Campbell, A. M., Monoclonal antibody technology. In Laboratory Techniques in Biochemistry and Molecular Biology 13, Elsevier, Amsterdam, 1984; Chames, P., et al., Direct selection of a human antibody fragment directed against the tumor T-cell epitope HLA-A1-MAGE-A1 from a nonimmunized phage-Fab library. *Proc. Natl. Acad. Sci. USA* 97:7969-7974, 2000; Uchanska-Ziegler, B., et al., Human single chain Fv fragments specific for NK cell receptors from phage display libraries. In Methods in Molecular Biology, Natural Killer Cell Protocols: Cellular and Molecular Methods (Campbell, K. S., and Colonna, M., eds.), pp. 219-237, Humana Press, Totowa, N.J., pp. 219-237, 2001; Hemmann, S. et al., Expression of the cysteine-rich extracellular domain of CD30 in Drosophila melanogaster S2 cells and selection of CD30-specific human single-chain Fv antibodies from a phage display library. Leukocyte Typing VII (D. Mason et al., eds.), pp. 463-466, 2002; Famulok M., Mayer G., Aptamers as tools in molecular biology and immunology. *Curr Top Microbiol Immunol;* 2243:123-36, 1999; Leval S. et al., GnRH Binding RNA and DNA Spiegelmers. A Novel Approach toward GnRH antagonism. *Chem Biol* March, 9:351-9, 2002).

In addition, the reagent according to the invention also produces an increased sensitivity in diagnosis and increased effectiveness in therapy. The increased sensitivity comes from the fact that twice as much reagent can bind to one and the same cell as with traditional reagents, with the increased amount of binding of the reagent leading to a stronger detection signal in the sample to be analysed. The increased effectiveness also comes from the fact that a large quantity of reagent can be taken up by a target cell so that it thus develops the corresponding effect on the target cell, for example by activating the complementary system or by the incorporation of toxins or radioactive isotopes which can ultimately kill the target cell.

The advantage of increased sensitivity or reliability in diagnosis can be achieved not only at the protein level but also at the nucleic acid level. A diagnosis based on nucleic acid analysis is also, with the use of the reagent according to the invention, less sensitive to the influence of mutations which may occur. If a target-cell specific e.g. tumour-specific nucleic acid is detected for example by means of specific interaction with a specific probe, as part of a polymerase chain reaction (PCR) for example, the occurrence of a single mutation can lead to the loss of the PCR signal if the mutation occurs in the recognition sequence of a specific primer used for the PCR. The simultaneous occurrence of this mutation event at two different points is extremely improbable, so that the reagent according to the invention can detect at least one section in the target cell specific nucleic acid, even if a recognition sequence for a primer at one of the two nucleic acid sections should be affected by a mutation.

The reagent according to the invention is particularly suitable for use in tumour diagnosis and/or therapy and in the diagnosis and/or therapy of inflammatory diseases such as in the early phases of HIV infection (Manetti R. et al., CD30 expression by $CD8^+$ cells producing type 2 helper cytokines. Evidence for large numbers of $CD8^+CD30^+$ T cell clones in human immunodeficiency virus infection. *J. Exp. Med.* 180:2407-2411, 1994; Del Prete G. et al., CD30, Th2 cytokines and HIV infection: a complex and fascinating link. *Immunol. Today* 16:76-80, 1995; Biswas P. et al., Cross-linking of CD30 induces HIV expression in chronically infected T cells. *Immunity* 2:587-596, 1995; Pizzolo G. et al., High serum level of the soluble form of CD30 molecule in the early phase of HIV-1 infection as an independent predictor of progression to AIDS. *AIDS* 8:741-745, 1994; Maggi E. et al., Activation of HIV expression by CD30 triggering in $CD4^+$ T cells from HIV-infected individuals. *Immunity* 3:251-255, 1995), hepatitis B infection (Fattovich G. et al., Serum levels of soluble CD30 in chronic hepatitis B virus infection. *Clin. Exp. Immunol.* 103:105-110, 1996) and auto-aggressive diseases such as rheumatoid arthritis (Gerli R. et al., High levels of the soluble form of CD30 molecule in rheumatoid arthritis (RA) are expression of CD30+ T cell involvement in the inflamed joints. *Clin. Exp. Immunol.* 102:547-550, 1995), Lupus erythematosus (Caligaris Cappio F. et al., Circulating levels of soluble CD30, a marker of cells producing Th2-type cytokines, are increased in patients with systemic lupus erythematosus and correlate with disease activity. *Clin. Exp. Rheumatol.* 13:339-343, 1995), primary biliary cirrhosis (Krams S M. et al., Elevations in IFN-gamma, IL-5 and IL-10 in patients with the autoimmune disease primary biliary cirrhosis: association with autoantibodies and soluble CD30. *Clin. Immunol. Immunopathol.* 80:311-320, 1996) and Wegener's granulomatosis (Wang G. et al., High plasma levels of the soluble form of CD30 activation molecule reflect disease activity in patients with Wegener's granulomatosis, *Am. J. Med.* 102: 517-523, 1997).

The reagent according to the invention is also suitable for detecting an immune reaction to a transplant or a graft-versus-host reaction and, for example, after intravenous application, for eliminating activated lymphatic cells which are causing the rejection or the graft-versus-host reaction (Pelzl S. et al., Soluble [1]CD30 as a predictor of kidney graft outcome. *Transplantation* January 15:73(1):3-6, 2003; Susal C. et al., Identification of highly responsive kidney transplant recipients using pretransplant soluble CD30. *Am Soc Nephrol* 13:1650-6, 2002; Nagahama M. et al., Serum levels of soluble CD30 in autologous peripheral blood stem cell transplantation, *J Cancer Res Clin Oncol* 126:101-6, 2000).

In a further preferred embodiment, the reagent covers at least one antigen binding domain as occurs with antibodies. To produce such reagents, the expert may choose from many methods from the state of the art, such as described by J. V. Gavilondo and J. W. Larrick in *Bio Techniques* 29:128-145, 2000.

In a further preferred embodiment, the reagent is an antibody, an antibody fragment, a chimerized antibody, a single-chain (sc)Fv fragment, an scT-cell receptor (TCR) fragment, a hybrid scFv/scTCR fragment, a DNA or RNA aptamer and/or a DNA or RNA Spiegelmer. The production of such reagents is possible for the expert without any problem, once he has recognised the epitope against which the reagent is to be directed.

In further preferred embodiments, the reagent according to the invention recognises the CD30 antigen. The CD30 antigen of humans is a glycoprotein with a molecular mass of 120 kD if this is determined by an SDS electrophoresis. What makes the CD30 antigen special is the fact that it is normally only found in the organism on activated T cell (Harmann D. et al., CD30 expression does not discriminate between human Th1- and Th2-type cells. *J. Immunol.* 156: 1387-91, 1996) and B cell blasts and tonsillar B cells (Dürkop H. et al., Expression of several members of the TNF-ligand and receptor family on tonsillar lymphoid B cells, *Br. J. Haematol.* 98:863-868, 1997), whilst it is expressed in a much higher concentration with a series of lymphoproliferative processes and with embryonal carcinomas of the testicles. The strongly CD30-positive malign lymphomas include primarily Hodgkin's lymphoma, the anaplastic large-cell lymphoma and also the acute or lymphomatous form of adult T cell leukaemia.

In a further preferred embodiment, the reagent reacts with a protein containing the amino acid sequence CEPDY as the core sequence of the epitope. The epitope in question occurs, amongst other things, twice in the CD30 antigen. The identification of an epitope that is recognised by the reagent according to the invention is easily possible using methods commonly used by experts, as is explained in more detail in the examples for the CEPDY epitope.

In a further preferred embodiment, the reagent reacts with a protein containing the amino acid sequence CEPDY (SEQ ID NO: 13) as the core sequence of the epitope. The epitope in question occurs, amongst other things, twice in the CD30 antigen. The identification of an epitope that is recognised by the reagent according to the invention is easily possible using methods commonly used by experts, as is explained in more detail in the examples for the CEPDY (SEQ ID NO:13) epitope.

In a particularly preferred embodiment, the reagent according to the invention is made from a cell such as that stored in the German Microorganisms Collection (Deutsche Sammlung für Mikroorganismen/DSM) under storage no. DSM ACC2548 with the designation DSZ1.

In a further preferred embodiment, the reagent is provided with a further component such as a toxin and/or a marking. The toxin is an advantage in the use of the reagent in therapy.

The reagent according to the invention is also preferably able to initiate the antibody-dependent cellular cytotoxicity (ADCC) against the cells carrying the target molecule; this is a major advantage over reagents which are taken from mice. The latter generally show no ADCC in the human organism and are thus per se of limited significance as a therapeutic active substance; however, it may be helpful additionally to attack the target cells, e.g. the tumour cells, by means of a toxin. Suitable toxins, which can be coupled to the reagent according to the invention for the purposes of therapy are known to the expert from the state of the art.

In a further preferred embodiment, the reagents are linked peptidically or via linker molecules with toxic proteins or with enzymes or proenyzmes, whereby the toxins are preferably present in the form of ribosome-inactivating proteins and the enzymes are preferably selected from the group of phosphodiesterases. In an alternative embodiment, the above mentioned reagents are covalent directly or via linker molecules or conjugated with photactivatable compounds or linked with radioactive isotopes, whereby the latter are selected preferably from the group consisting of indium, iodine, yttrium, technetium, rhenium, copper and lutetium. The link can be made, for example, using chelate formers or via photochemical activation processes (cf. WO 94/04189).

The insertion of a marking into the reagent according to the invention can on the one hand have advantages in terms of diagnostics—in order, for example, to increase the sensitivity of detection—and on the other hand may bring advantages in tumour therapy, for example. By affixing a marking, such as an alpha emitter, the tumour tissue can, after binding of the marked antibody, be selectively damaged by means of the alpha emitter and thus fought. $^{131}$J in particular can be considered as a marker for diagnostics.

The present invention also relates to a cell which produces the reagent according to the invention. These include for example recombinant host cells which carry/contain or produce a nucleic acid and which are suitable for example for the specific detection of target cell nucleic acids. In addition, this also includes a cell which produces a reagent that binds to the target at protein level. Such cells include recombinant cells into which genes are incorporated which are responsible for the formation of the suitable antigen-binding domain in the reagent according to the invention. The cloning of the suitable V-region genes and their incorporation into host cells is known to the expert from the state of the art (cf. e.g. J. V. Gavilondo and J. W. Larrick (above)); suitable cells are also antibody-secreting myeloma hybrids.

In a further preferred embodiment, the cell contains a recombinant nucleic acid which, coded for the reagent or a part thereof, especially for the protein portion of the reagent which is involved in target recognition, preferably therefore forms the antigen binding site.

A further preferred embodiment is a cell which shows the essential properties of the cell saved at the DSM under storage number DSM ACC2548. The "essential properties" are the ability of the cell to produce a reagent according to the invention even if other properties of the cell as stored under the given number have been changed such as, for example, growth behaviour, the resistance markers and so on. The essential features of the cell according to the invention also include the ability to form very high quantities of reagent, especially up to around 20 μg reagent/ml when conventional cell culture methods are used and up to 500 μg reagent/ml if so-called hollow fibre fermenters are used (UniSyn Technologies Inc., Hopkinton, Mass., USA). Furthermore, a characteristic feature of the cell consists of growing stably in the absence of a selection marker such as G418 over an unlimited period of time without losing the ability of producing the reagent in large quantities. The cell according to the invention has considerable advantages over cells known from the state of the art in that the cell according to the invention can be cultivated in large quantities in a simple, cheap way without the addition of selection markers such as G418 to the medium being necessary. The cell according to the invention is surprisingly also stable in the absence of corresponding selection markers, which means that the reagent according to the invention is produced in consistently large quantities and high quality even after a long cultivation period.

The present invention also relates to a method of diagnosis especially of cancer and inflammatory diseases, whereby with this method a sample from the test person is brought into contact with the reagent according to the invention and the extent of the reaction of the reagent with the sample is determined. A sample is taken from the patient and, depending on the reagent to be used, prepared accordingly. If the sample is used in nucleic acid analysis or diagnosis, the nucleic acid is isolated from the material and used in normal methods and processes of nucleic acid analysis, such as PCR, for example. If specific primers are used which specifically recognise target cell nucleic acids and PCR is carried out, it can be determined whether the sample in question contains, for example, a target cell specific nucleic acid. The methods for carrying out the PCR and detecting PCR products are known to the expert. Alternatively, the sample can also be treated with a reagent which detects the target at protein or carbohydrate or lipid level. Preferably, reagents are used for this purpose which bear a marking, such as an enzyme marking for example, which allows the detection of the reagent by a dye converted by them, which precipitates at the place of origin and thus marks the location of the reagent that has reacted specifically with the tissue sample. Suitable groups for conjugating to the reagent are known to the expert. Alternatively, the reagent can also be provided with a fluorescent group and detected using fluorescence detectors. In a further preferred embodiment, the tumour tissue is detected in vivo using scintigraphy. This method can also be used to directly follow the course of a tumour therapy, in that the method provides information as to how far the tumour has spread or reduced in size.

Preferably, the reagent according to the invention is used for the treatment of cancer and inflammatory diseases, whereby lymphomas in particular can be treated. In a particularly preferred embodiment, CD30-positive lymphoma are treated using the reagent according to the invention, whereby in particular Hodgkin's lymphoma, anaplastic large-cell lymphoma and/or the acute or lymphomatous form of adult T-cell leukaemia can be treated using the reagents according to the invention.

In therapy, preferably 1-1000 mg reagent/m$^2$ body surface is used, and most preferably 1-400 mg reagent/m$^2$ body surface. In a further preferred embodiment, the reagent is dispensed intravenously, whereby other methods of dispensation can be considered, depending in particular on the location of the tumour.

Finally, the present invention provides a test kit which is suitable in particular for the diagnosis of cancer, especially Hodgkin's lymphomas, anaplastic large-cell lymphomas and/or acute or lymphomatous forms of adult T-cell leukaemia and inflammatory diseases as well as transplantation-related immune reactions. The kit contains, in addition to the reagent according to the invention, further usual materials such as buffers, solutions for sample preparation, solutions for detecting the reagent, including instructions for use for carrying out the test.

EXAMPLES

Example 1

Production of the Antibody According to the Invention

A chimerized CD30 antibody, as produced by the stored cell line DSZ1, is based on the constant regions of the human IgG1κ chain and the variable regions which code the antigen binding site for the CEPDY epitope of CD30. The latter V genes can be isolated with the following primers:

(SEQ ID NO:1)
A-$C_\kappa$: 5' AGATGGATACAGTTGGT;

(SEQ ID NO:2)
A-$C_H$1: 5' GGGGCCAGTGGATAGAC;

(SEQ ID NO:3)
$B_{Not1}$: 5' GCGCGGCCGCGGAGG;

(SEQ ID NO:4)
$C_{Not1}$: 5' GCGCGGCCGCGGAGGCCCCCCCCCCCCCC;

(SEQ ID NO:5)
D-$C_{\kappa EcoRI}$: 5' GGAATTCGGATACAGTTGGTGCAGC;

(SEQ ID NO:6)
D-$C_H I_{EcoRI}$: 5' GGAATTCGTGGATAGACAGATGGG;

(SEQ ID NO:7)
E-$_{\kappa Sal1}$: 5' GATCGTCGACGGAAATGCATCAGACCAGCATGGGC;

(SEQ ID NO:8)
E-$H_{Sal1}$: 5' CATAGTCGACAATACGATCAGCATCCTCTCCACAG;

(SEQ ID NO:9)
F-$_{\kappa Not1}$: 5' ATCAGCGGCCGCACTTAACAAGGTTAGACTTAGTG;

(SEQ ID NO:10)
F-$H_{Not1}$: 5' GATA GCGGCCGCATGCATTTAGAATGGGAGAAGTTAGG;

whereby the isolated region includes the rearranged genomic VDJ region, including the original signal peptide, signal peptide intron and the authentic splice points. A $V_L$ and a $V_H$ clone without mutations or irregular sequences which derive from the myeloma fusion cell line were selected for cloning into the eukaryotic expression vectors pUHWκ and pUHWγ (available from Dr. U. Weidle, Roche, Penzberg), whereby they contained the human κ or $C_H$ 1-3 gene segments. After stable cotransfection into the mice myeloma cell line Sp2/0-Ag14 and selection with G418, the transfectants secreted between 50 ng/ml-150 ng/ml of the antibody. For cleaning and conjugation of this chimerized antibody, this antibody was produced in large quantities by the transfected cells being placed in a hollow fibre system. After further selection with the "limiting dilution" method, partly using G418, the cells produce approx. 20 μg/ml in a conventional cell culture. In hollow fibre systems, this value is not less than 100 μg/ml and may reach up to 500 μg/ml.

The antibody against CD30 according to the invention comes from rearranged genomic variable $V_H$DJ and $V_L$J segments and a constant region of the human IgG1 heavy chain and the light chain of the κ type. Typically, chimeric antibodies are constructed in that the cDNA which codes for the $V_H$DJ and $V_L$J domains, is fused to Cγ and Cκ/λ, gene segments (cf. Hanai, N. et al., Recombinant antibodies against ganglioside expressed on tumor cells. *Cancer Chemother Pharmacol* 46-(Suppl):13-7, 2000; Hoogenboom, H. R. et al., Cloning and expression of a chimeric antibody directed against the human transferrin receptor. *J. Immunol* 144:3211-7, 1990; Krishnan, I. S. et al., Chimerization of Mu-9: a colon-specific antigen-p antibody reactive with gastrointestinal carcinomas. *Cancer* 80 (Suppl), 2667-74, 1997; Liu, A. Y., Chimeric mouse-human IgG1 antibody that can mediate lysis of cancer cells, *Proc. Natl Acad Sci USA* 84:3439-43, 1987; Shitara, K., A mouse/human chimeric anti-(ganglioside GD3) antibody with enhanced anti-tumor activities. *Cancer Immunol Immunother* 36:378-80, 1993). In most cases, the cDNA is amplified for the variable domains by means of PCR using degenerated primers (cf. Dübel, S., Isolation of IgG antibody Fv-DNA from various mouse and rat hybridoma cell lines using the polymerase chain reaction with a simple set of primers. *J Immunol Methods* 175:89-95, 1994; Orlandi, R. et al., Cloning immunoglobulin variable domains for expression by the polymerase chain reaction. *Proc Natl Acad Sci USA* 86:3833-7, 1989) and the ends of the rearranged gene segments are modified with non-authentic amino acid residues. This means that these cDNA-based constructs no longer have the original link between the peptide-V(D)J-C exon/intron, whereby this can lead to low protein expression rates (cf. Liu et al., Production of a mouse-human chimeric monoclonal antibody to CD20 with potent Fc-dependent biologic activity. *J Immunol* 139:3521-6, 1987) or even to a loss of the expression of the chimeric light chain. In contrast to this, in the present case the genomic sequence of the variable domain of a genomic sequence was used, whereby this lead to a reliable production of the protein in very large quantities.

Example 2

Binding Properties, Specificity and Epitope Mapping of an Antibody Secreted by the Cell Line According to the Invention In flow cytometry, this antibody shows a specific binding with $CD30^+$ cell lines, but does not react with $CD30^-$ cell lines.

Figure 1:
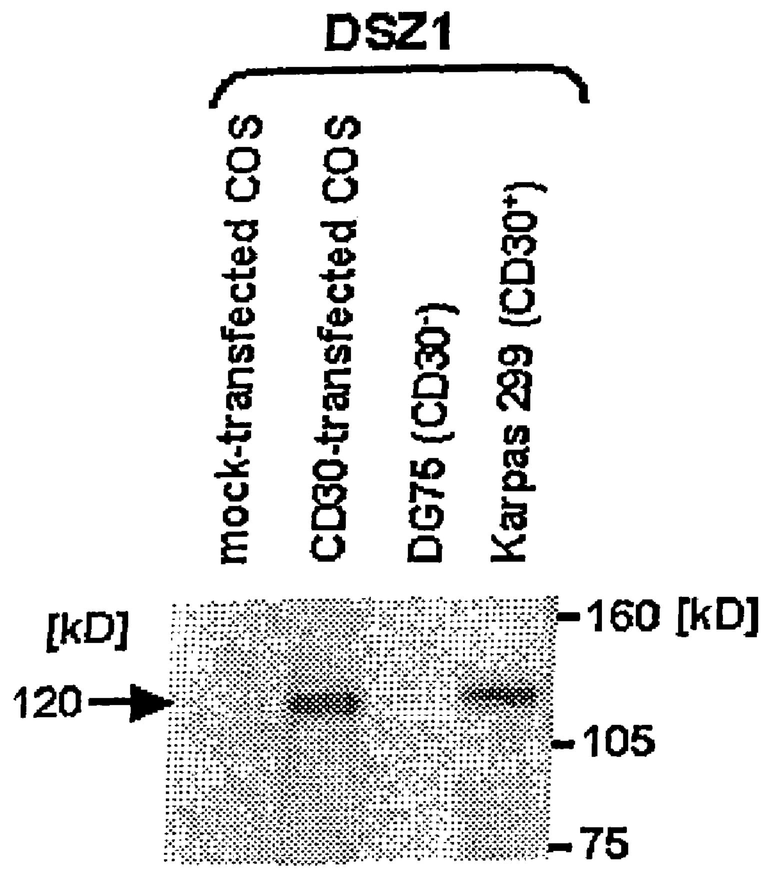
FIG. 1 shows a Western Blot with the antibody according to the invention. The antibody recognises the CD30 antigen which is indicated by the band at 120 kD and is expressed only by the $CD30^+$ cells Karpas 299 and CD30-transfected COS cells, but not by the $CD30^-$ cell line DG75 and mock-transfected COS cells.

In addition, this antibody in Western Blot analyses shows a binding to an antigen with the same molecular weight in the lysates of $CD30^+$ cell lines and CD30 transfected COS cells. In contrast to this, no protein was detected by the antibody in lysates from $CD30^-$ cell lines (see FIG. 1).

The immunohistological dye pattern with the antibody according to the invention produces a strong colouring of the Hodgkin's and Reed-Sternberg (HRS) cells in 32/32 cases of classic HL, a strong colouring in 10/10 cases of tumour cells of ALCL and in 6/6 cases of embryonal carcinomas of the testicles, whilst only a few perifollicular lymphoid blasts in hyperplastic tonsils showed a weak marking. The antibody marked no tumour cells in two cases of lymphocyte-predominant HL (LPHL), in four cases of follicle centre lymphoma, in three cases of satellite cell lymphomas, in seven cases of B-CLL, in two cases of diffuse, large-cell B-cell lymphoma of the centroblast variant, in three carcinomas of the stomach, in four carcinomas of the pancreas, in six carcinomas of the colon, in three kidney carcinomas and four adenocarcinomas of the lungs and also in normal tissue from the liver, stomach, colon, kidneys, pancreas and testicles.

Figure 2:
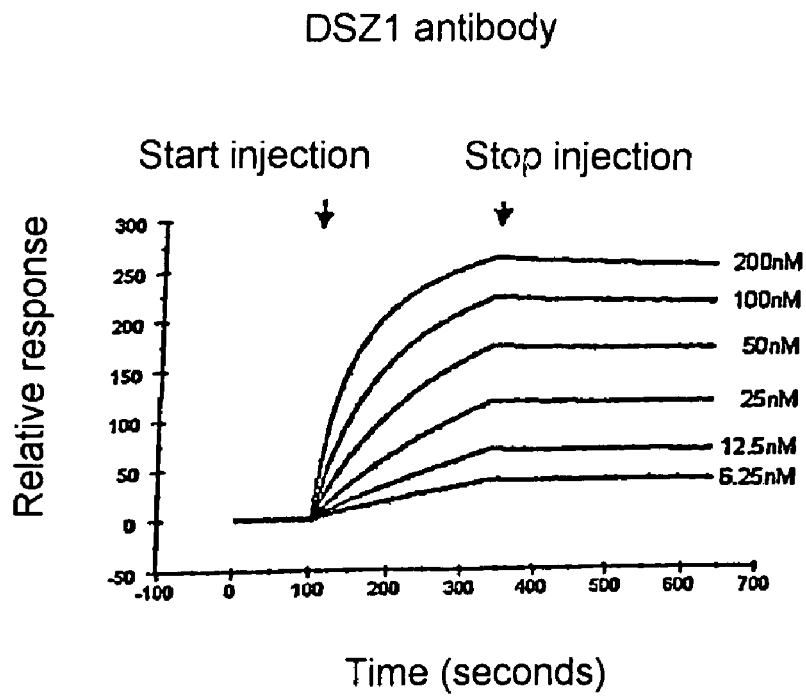
FIG. 2 shows a surface plasmon resonance analysis of the antibody according to the invention. The blot shows the binding of the antibody according to the invention in various concentrations (18.75 nM-600 nM) to the immobilised extracellular domain of CD30 which was expressed in Schneider 2 Drosophila cells.

Determining the binding affinity ($K_D$) of the antibody according to the invention which is produced by the cell line DSZ1 with the storage no. DSM ACC2548 by means of surface plasmon resonance showed that the antibody binds to the recombinant extracellular domain of CD30 with a comparatively high affinity of $K_D$=7.82×$10^{-10}$ M±1.04×$10^{-10}$ M, as shown in FIG. 2.

Figure 3:
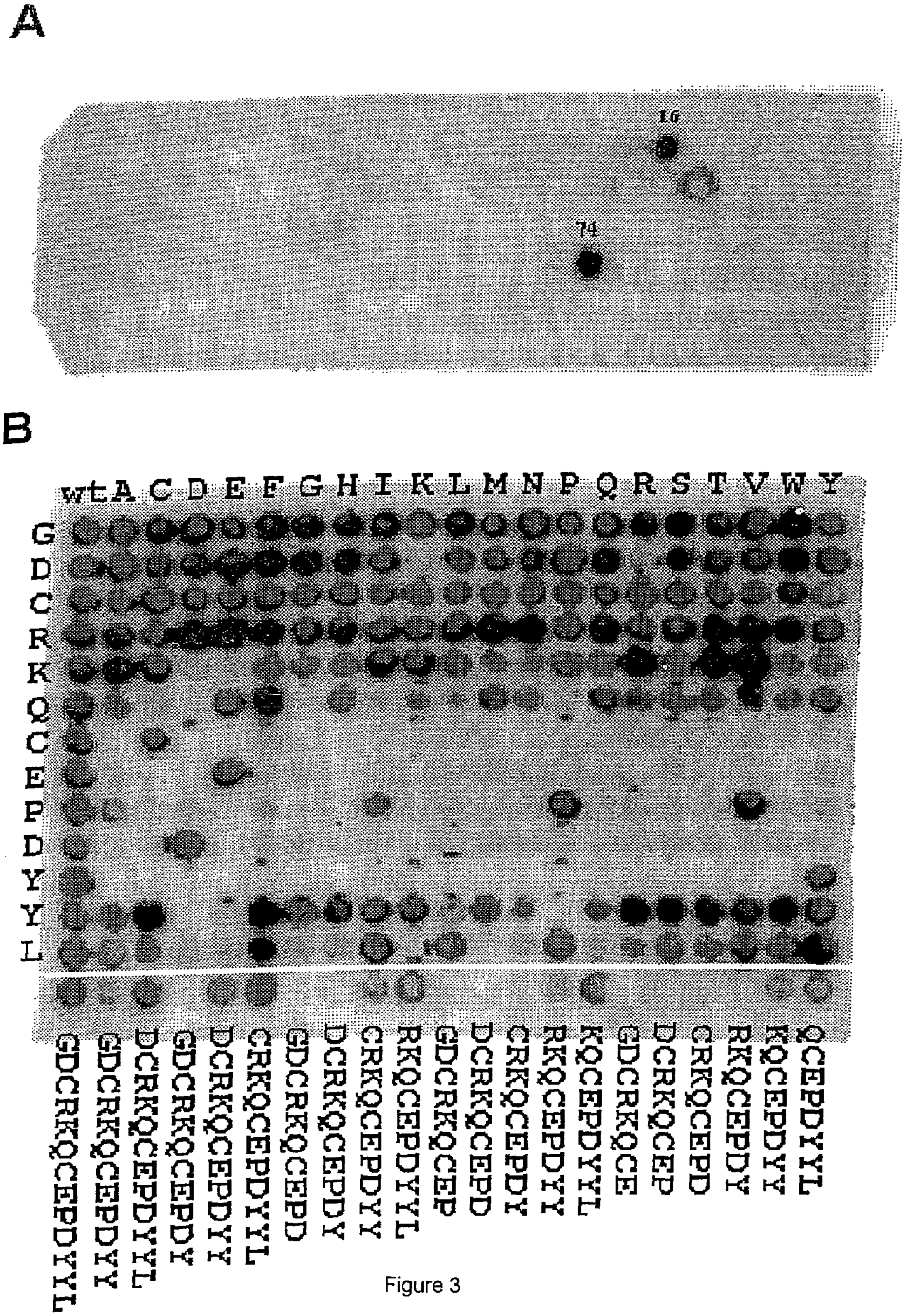
FIG. 3 shows the epitope analysis of the antibody according to the invention.

The mapping of the epitope to which the antibody according to the invention binds showed that this binds to a peptide sequence which occurs twice in the extracellular domain of CD30. The antibody secreted by the cell line DSZ1 according to the invention showed two strong signals with peptides derived from CD30 (cf. FIG. 3): Spot 16 (with the sequence $^{64}$DCRKQCEPDYYLD$^{76}$ (SEQ ID NO: 11)) and Spot 74 ($^{238}$GDCRKQCEPDYYL$^{250}$ (SEQ ID NO:12)). An extensive mapping of the epitope using substitution analysis gave the amino acid residue CEPDY (SEQ ID NO:13) as the core sequence for the interaction. Both epitopes bind the antibody secreted by the cell line according to the invention and the binding was not lost if only one of the epitopes was mutated, whilst mutation in both epitopes led to the loss of the antibody recognition.

Example 3

Antibody-Dependent Cellular Cytotoxicity (ADCC) of an Antibody Secreted by the Cell Line According to the Invention In order to determine the ability of the antibody secreted by the cell line according to the invention to produce the antibody-dependent cellular cytotoxicity (ADCC), the $CD30^+$ lines L540 and HDLM2 derived from HL, the $CD30^+$ cell lines Karpas 299 and JB6 derived from ALCL, and also the lymphoid $CD30^-$ cell lines DG75 and SUP-T1 were marked with $^{51}Cr$ and/or CMFDA. Together with the stimulated human peripheral blood lymphocytes (LAK and CIK protocol) and monocyte cells as effector cells, the antibody according to the invention induced a significant specific lysis of the $CD30^+$ target cell lines L540, HDLM2, Karpas 299 and JB6 (25%, 12%, 10% and 5% respectively, see FIG. 4). The plateau of the cell lysis was achieved with a concentration of 500 ng/ml antibody. The ADCC induced lysis of the $CD30^+$ cells was achieved with an effector-target ratio of 5:1. Depending on its binding properties, the antibody according to the invention did not lead to an induction of the ADCC effect on $CD30^-$ cell lines.

Example 4

Cloning of a Cell Line which Produces an Antibody Secreted by the Cell Line According to the Invention The initially produced cells which create the antibody according to the invention produced antibodies in a concentration of 100-150 ng/ml. By repeated subcloning of the cells on 96-hole perforated plates with the addition of G418 (1.2 mg/ml) and subsequent testing of the clone as regards its production properties (antibody concentration in the culture supernatant by means of ELISA and immunocytological determination of the percentage of the antibody-producing cells), it was finally possible to present clones of these transfectants which secreted 10-20 μg/ml of the antibody.

To produce larger quantities of antibodies, the cells were cultivated in hollow fibre systems made by UniSyn Technologies Inc., Hopkinton, Mass., USA with permanent circulation of the medium in the intracapillary space. In these systems, an antibody concentration of up to 500 μg/ml was achieved.

The ELISA for determining the antibody concentration was carried out as follows:

Coating of a 96-microtitre plate with a goat-anti-human IgG (SIGMA, #I-2136) in a concentration of 2 μg/ml in a volume of 100 μl with a two-hour incubation at room temperature or twenty-four-hour incubation at 4° C. Blockage of the plate surface (200 μl 3% BSA, 0.1% (v/v) Tween 20 in PBS; at least 2 hours, room temperature). Triple washing with 0.1% (v/v) Tween 20 in PBS. Application of 100 μl of the concentrated or pre-diluted cell culture supernatant; incubation: 1 hour at room temperature. Application at the same time of a dilution series of a human immunoglobulin preparation with a known concentration (Sigma human IgG1, kappa #1-3889). Triple washing as described above. Detection of the immunoglobulin using an alkaline phosphatase-conjugated goat-anti-human IgG (SIGMA, #A-9544; incubation: 1 hour at room temperature). Triple washing (see above). Then apply substrate buffer (prepared from tablets, Sigma FAST™ p-Nitrophenyl Phosphate Tablet sets #N-2770/#N-1891) and measure at 405 nm after ten-minute incubation at room temperature. Evaluation is only carried out on those samples which show an extinction in the area in which the extinction of the standard carried shows a linear increase.

Execution of the immunohistology and cytology according to Cordell (Cordell J. et al, Immunoenzymatic labelling of monoclonal antibodies using immune complexes of alkaline phosphatase and monoclonal anti-alkaline phosphatase (APAAP complexes), *J. Histochem. Cytochem.,* 32:219-229, 1984). The cell line obtained in this way was stored at the German Microorganisms Collection under no. DSM ACC2548.

The invention claimed is:

1. A reagent that binds CD30, wherein the reagent is (1) an antibody produced by the cell DSZ1 stored at the German Microorganisms Collection (DSM) under the number DSM ACC2548; (2) a humanized version of the antibody of (1); or (3) a binding fragment of either the antibody of (1) or the humanized antibody of (2).

2. The reagent of claim 1, which is linked to a toxin or a fluorescent group.

3. The reagent of claim 2, linked directly or via a linker molecule covalently or conjugated with a photoactivatable compound.

4. The reagent of claim 1, linked peptidically or via a linker molecule to a toxic protein, an enzyme, or a proenzyme.

5. The reagent of claim 4, wherein the toxic protein is a ribosome-inactivating protein.

6. The reagent of claim 4, wherein the enzyme is a phosphodiesterase.

7. The reagent of claim 1, linked directly or via a linker molecule covalently or conjugated with a radioactive isotope.

8. The reagent of claim 7, wherein the radioactive isotope is selected from the group consisting of indium, iodine, yttrium, technetium, rhenium, copper and lutetium.

9. A composition comprising the reagent of claim 1.

10. A kit for diagnosing CD30-positive neoplasies and inflammatory diseases, comprising the reagent of claim 1 and instructions for performing the diagnosis.

11. An isolated cell, stored at the DSM under the no. DSM ACC2548.

* * * * *